United States Patent [19]

Rudolph et al.

[11] Patent Number: 4,486,114

[45] Date of Patent: Dec. 4, 1984

[54] INTERCHANGEABLE COMPONENT IDENTIFICATION SYSTEM

[75] Inventors: Dale C. Rudolph, Parker; Michael D. Ray, Denver, both of Colo.

[73] Assignee: Technicare Corporation, Solon, Ohio

[21] Appl. No.: 191,577

[22] Filed: Sep. 29, 1980

Related U.S. Application Data

[62] Division of Ser. No. 972,435, Dec. 22, 1978, Pat. No. 4,244,227.

[51] Int. Cl.$^3$ .............................................. B25G 3/00
[52] U.S. Cl. ...................................... 403/27; 403/161
[58] Field of Search .................. 403/27, 161, 162, 163

[56] References Cited

U.S. PATENT DOCUMENTS

| | | | |
|---|---|---|---|
| 3,710,674 | 1/1973 | Tabor | 403/162 X |
| 3,816,853 | 6/1974 | Elson | 403/163 X |

Primary Examiner—Andrew V. Kundrat

[57] ABSTRACT

Disclosed is a system for identifying which one of a plurality of interchangeable transducer heads is connected with an ultrasonic scanner. The system includes a unique impedance mounted on each transducer head and an impedance determining circuit in the scanner for determining the impedance of the interconnected transducer head. The impedance determination circuit is connected to a character generator for producing an alpha-numeric representation of the transducer head designation along the margin of a cathode ray tube on which an ultrasonic image is displayed. Also disclosed is an improved resolver mounting in which a cylindrical axle is used as a pivot pin between two scan arms of the ultrasonic scanner. A potentiometer for resolving the angle between pivotally connected arms is mounted on one arm with its shaft resiliently connected with the axle for rotation with the axle and other scan arm.

2 Claims, 8 Drawing Figures

INTERCHANGEABLE COMPONENT IDENTIFICATION SYSTEM

This is a division of application Ser. No. 972,435, filed Dec. 22, 1978, and now U.S. Pat. No. 4,244,227.

BACKGROUND OF THE INVENTION

This invention relates to interchangeable component identification systems and more particularly to an electronic system for indicating which one of a plurality of interchangeable probes or work elements is interconnected with an overhead arm assembly.

The invention is particularly applicable for use with medical ultrasonic diagnostic apparatus and will be described with particular reference thereto. However, it will be appreciated that the invention has broader applications in other fields in which work elements are regularly interchanged.

In ultrasonic medical diagnostics, images of internal areas of a patient are obtained by transmitting ultrasonic energy into the patient and monitoring the ultrasonic echoes. A planar slice of the patient is most commonly examined. The examination is typically accomplished by utilizing a single probe element which both transmits ultrasonic energy and receives the echoes. By monitoring the position and orientation of the probe as it is moved to various points along the line of intersection between the planar slice and the surface or body of the patient, signal processing equipment can transform the position data and echoes into a representation of the examined planar slice. An example of such processing equipment is shown in U.S. Pat. No. 3,036,390.

The structural characteristics of the transducers determine the application to which they are best suited. Accordingly, it is advantageous for the operator to change transducer heads for different types of examinations. For example, transducers with higher or lower sensitivity may be desired. As another example, the diameter of the transducer is a determining factor of the depth within the patient at which ultrasonic waves are most precisely focused, i.e. focal length.

Providing an operator with a plurality of interchangeable transducer heads leads to difficulty in identifying the transducers. This difficulty is compounded when the need for identification arises during a scan when the transducer head is in a relatively inaccessible position and being moved or after a scan when viewing a photograph of the ultrasonic image.

The ultrasonic probe is normally carried by an arm assembly defined by a plurality of movable, jointed arms. These arms are constrained to movement within a single plane, i.e., the plane of the patient slice which is to be examined. Prior arm assemblies have generally comprised a plurality of pivotally interconnected arms, such as is shown in U.S. Pat. No. 3,924,452, a plurality of linearly, slideably jointed arms, such as is shown in U.S. Pat. No. 3,036,390 or a combination of these two arrangements. The designs of these and other prior arm assemblies have been such that there were problems in accurately selecting the plane of examination. Some prior assemblies were also lacking in adjustment flexibility and required movement of the patient for purposes of changing the plane of examination.

To determine the position and angular orientation of the transducer probe at the end of the arm assembly, conventionally each pivot between the arms is associated with a variable resistor or potentiometer. The variable resistor is interconnected with the arms such that as the arms pivot relative to each other the resistance changes. By monitoring the resistance or change in a voltage applied across the variable resistor, the orientation of the probe may be determined. See "Ultrasonic Contact Scanner for Diagnostic Application", J. H. Holmes et al., American Journal of Medical Electronics 1965.

Interconnecting the potentiometer with the arms has been accomplished with a series of belts and pulleys, see for example, U.S. Pat. No. 3,924,452. But such a system is bulky and subject to belt slippage and breakage. The interconnected has also been tried by locating the potentiometer at the pivot with the shaft of the variable resistor forming part of the pivot mechanism. This interconnection, however, places excessive forces on the shaft and bearing of the variable resistor causing frequent variable resistor failure.

In practical application, doctors often wish to obtain and view more than one planar slice of a patient. These plural slices are most reliably diagnosed if they are parallel and spaced apart by known increments. In prior arm assemblies, especially those which required patient movement for changing the plane of examination, movement to parallel planes was usually arduous and imprecise. Even in the selection of an initial or first plane, alignment of the plane of interest in the patient and the scan plane of the arm was often haphazard and imprecise.

Another problem encountered with prior arm assemblies is that they have been awkward to operate. In some prior assemblies, the scan arms have not been counterweighted or if counterweighted, they have been done so in a crude and inaccurate manner. Often the arms have been constructed of lightweight materials and without proper counterweighting which required the operator to exert different amounts of force to produce the same scanning movement in different portions of the scan plane. This problem resulted in undesired degradation of the visual image being produced.

The present invention contemplates new and improved apparatus which overcomes all of the above referred to problems and others and provides an overhead arm and scanning assembly which is flexible, easy to use, and precisely oriented.

SUMMARY OF THE INVENTION

In accordance with the present invention, there is provided a multijointed overhead arm assembly having a first arm pivotally mounted adjacent one end to a base with a second arm pivotally mounted adjacent one end thereof to the other end of the first arm. A dynamic counterbalancing assembly is operably associated with the first and second arms for applying a counterbalancing force to the first arm about its pivotal connection with the base and which counterbalancing force varies with the angular orientation of the second arm relative to the base. A static counterbalancing may also be provided for the first arm which varies in counterbalancing force in response to the angular orientation of the first arm relative to the base.

In accordance with another aspect of the present invention, a third arm is pivotally mounted adjacent one end thereof to the outermost end of the second arm. The third arm is adapted to support dependent equipment at the distal end thereof and may include orientation means for constraining the third arm movement to a fixed angular orientation relative to the base.

In accordance with still another aspect of the present invention, a manipulation means is operably associated with the distal end of the third arm which constrains a scan arm or other work element to motion through a single predetermined plane. Positioning means associated with the manipulation means facilitates locating the precise position of the plane.

In accordance with yet another aspect of the invention, displacement means allow selective adjustment of the scan arm or other work element from motion through an initial plane to motion through other planes spaced from and parallel to the initial plane.

Another aspect of the invention is the provision of means for identifying the transducer head which is interconnected with the arm assembly. In accordance with a more limited aspect, identification of the transducer head is provided on the same screen on which the ultrasonic image is produced.

In accordance with a further aspect of the invention, the potentiometer is located at the pivot, but high failure rates are avoided by resiliently coupling the potentiometer to a pivot pin.

Among the benefits derived from the present invention is the ease and accuracy with which a work element, such as an ultrasonic probe or the like, can be positioned relative to a patient or other target. A probe mounted on a scan arm assembly which is constrained to planar motion can have its plane of motion rotated or incrementally displaced. As a result it is possible to produce a series of cross-sectional images of a patient precisely along preselected planes and to have each of the series of images represent parallel planes with known interplanar displacement.

A further benefit of the present invention resides in the simplicity and ease with which the equipment may be moved and positioned. A work element can be smoothly movable by an operator since the overhead arm assembly itself can be easily and continuously positioned to accomodate the work element relative to its target. Improved scanning images are obtained from ultrasonic equipment mounted on the subject overhead arm assembly due to a lessening of operator fatigue and the provision of smooth, effortless scanning and positioning movement.

Another benefit of the present invention is easy identification of the transducer head. Identification can be made during a scan without interrupting the scan. Further, photographs of the ultrasonic image show the transducer head which produced the image.

One more benefit is extended life of potentiometers used to indicate the position and angular orientation of the transducer head.

Yet other benefits will become readily apparent from an understanding of the invention as described hereinafter with reference to the preferred embodiment.

BRIEF DESCRIPTION OF THE DRAWINGS

The invention may take physical form in certain parts and arrangements of parts, a preferred embodiment of which will be described in detail in this specification and illustrated in the accompanying drawings.

FIG. 6 is an enlarged view of a portion of the displacement assembly shown in FIG. 1;

DESCRIPTION OF THE PREFERRED EMBODIMENT

Figure 1:
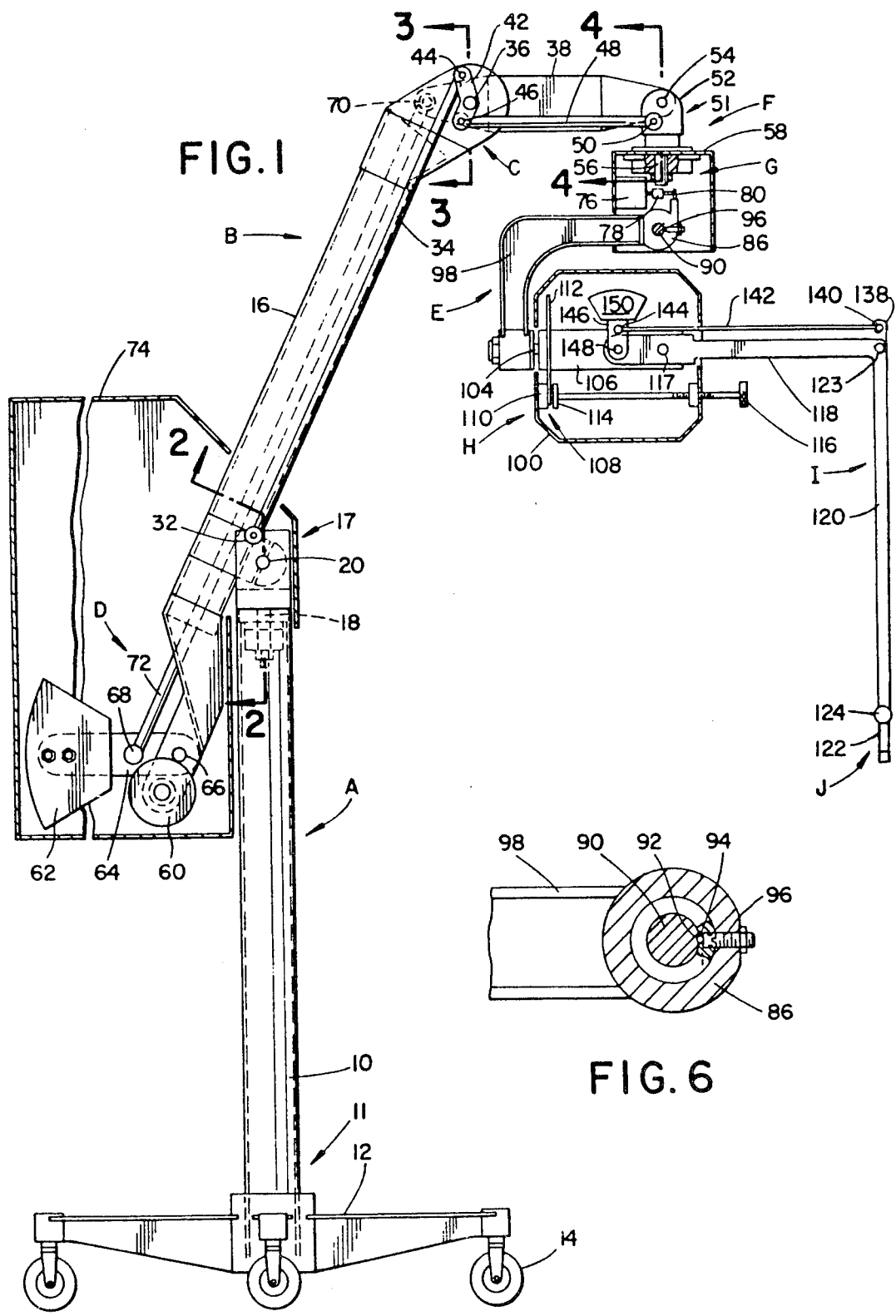
FIG. 1 is a side elevational view of the overall overhead arm assembly with portions of some components removed for ease of illustrating the invention.

Referring now to the drawings wherein the showings are for purposes of illustrating the preferred embodiment of the invention and not for the purpose of limitation, the figures show an overhead arm assembly used in conjunction with ultrasonic diagnostic apparatus. While this is the preferred use for the subject invention, it will be appreciated that it can be readily adapted to use in any number of other environments. More particularly, FIG. 1 shows a base A having an overhead arm assembly B mounted thereto. This assembly generally includes an orientation means C, a counterweight assembly D and a manipulating assembly E. The orientation means controls the suspended orientation of manipulating assembly E relative to base A. Associated with the manipulating assembly is a rotational coupling F, a horizontal incremental displacement assembly G, an angular orientation selection means H and a multijointed scan arm assembly I. Detachably connected to the scan arm assembly is one of a plurality of interchangeable transducer heads J. The scan arm assembly is desirably constrained for motion within a single scan plane and the manipulation assembly allows this scan plane to be rotated about a vertical axis in a yaw plane, displaced linearly perpendicular to the plane of FIG. 1 and rotated about a horizontal axis in a roll plane.

Figure 8:
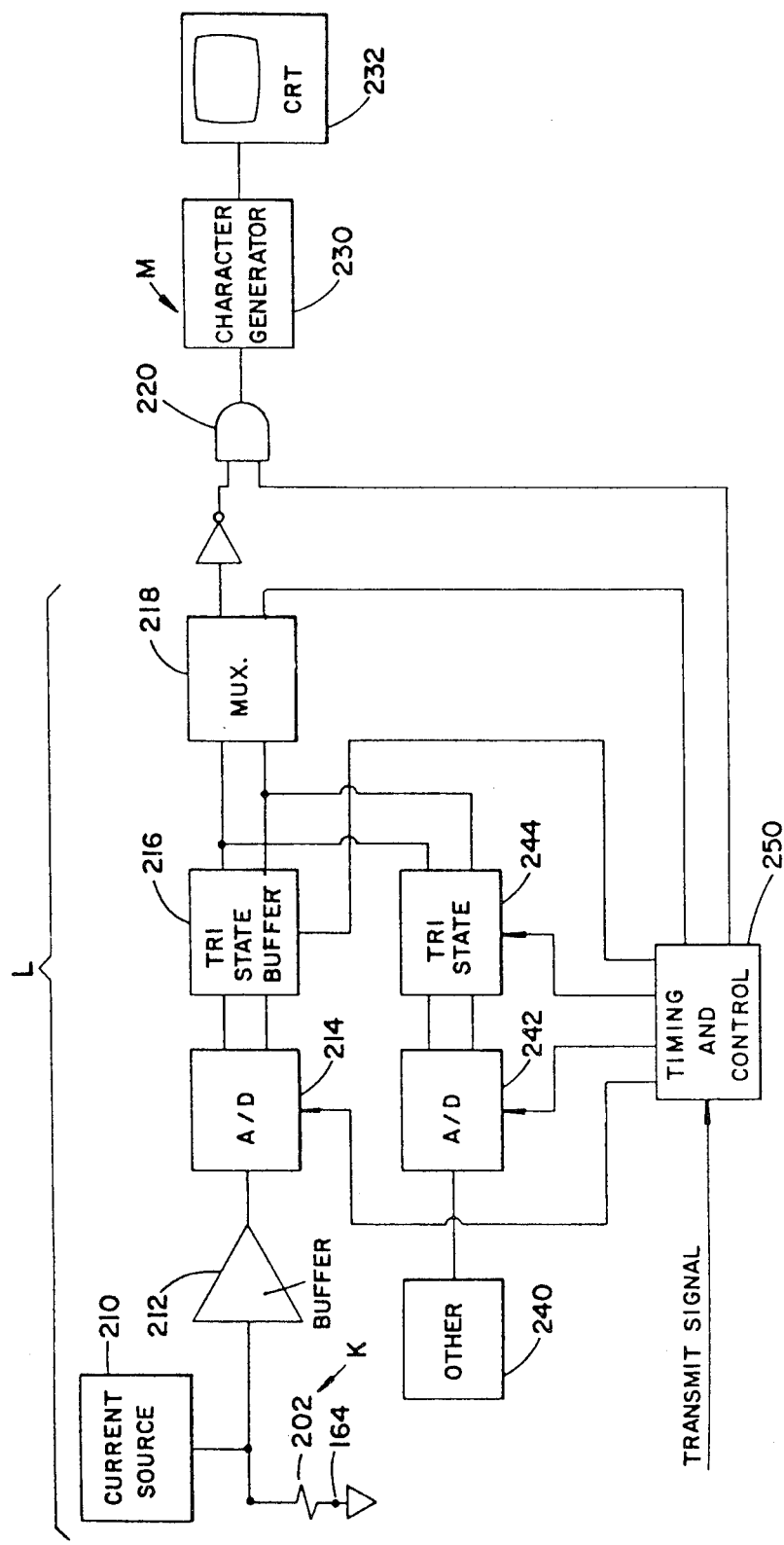
FIG. 8 is a circuit diagram of a transducer head identification system.

A transducer head identification system, illustrated in FIG. 8 identifies which of the plurality of transducer heads is attached. The system includes an identification means K mounted on each transducer head which has an identifying impedance, an impedance determination means L for determining the identifying impedance and a display generating means M for generating an alphanumeric display identifying the transducer head.

With reference to FIG. 1, it will be seen that base A includes an elongated vertical column 10 which is securely mounted relative to the floor. Positional stability for column 10 may be provided by many alternative arrangements although the preferred embodiment contemplates one end of the column being fixedly attached by convenient means as at 11 to a base plate 12. The base plate is provided with suitable castors 14 to enable the overhead arm assembly and attendent equipment to be easily brought to the patient or object to be examined.

Arm assembly B which includes a first or main arm 16 is mounted adjacent the other end of column 10 at a first joint generally designated 17 having two degrees of freedom. The first degree of freedom is derived from rotational movement about a pivot pin 18 in what is termed as a yaw plane and the second degree of movement is derived from rotational movement about another pivot pin 20 in what is termed as a pitch plane.

Figure 2:
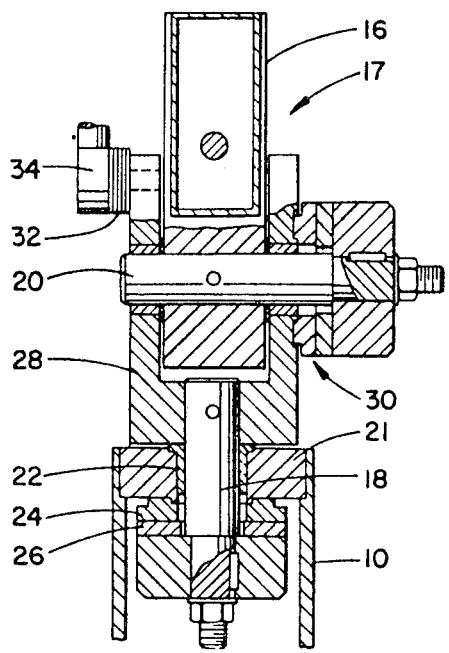
FIG. 2 is a cross-sectional view taken along lines 2—2 of FIG. 1.

FIG. 2 shows the details of first joint 17. Mounted at the top or uppermost end of column 10 is an end cap 21 which receives a bushing 22 which, in turn, receives and locates pin 18 in a generally vertical disposition. Attached to the underside of end cap 21 is a first brake plate 24 adapted to frictionally cooperate with a second brake plate 26 conveniently affixed to pin 18. The first friction brake arrangement defined by brake plates 24, 26 is designed to have a high torque, yet require a small amount of space. This type of brake arrangement allows first arm 16 to be moved through a continuum of positions as may be desired. A tooth-type of brake assembly could also be advantageously employed if desired. Such a brake would be somewhat more restrictive in that it would allow the arm to assume a large, but finite number of positions.

Pin 18 is attached to a clevis member 28 which is designed to receive appropriate bushings for receiving and supporting pin 20 in a generally horizontal disposition. Pin 20 is rigidly attached to main arm 16 so that it rotates therewith. A second brake arrangement generally designated 30 provides braking movement of the main arm 16 relative to base A. Brake 30 is located between pin 20 and clevis member 28 and is constructed in a manner similar to the first brake described hereinabove. Clevis member 28 carries a second pivotal connection 32 to mountingly accommodate a linear link 34 for a first orientation connecting means which comprises an element of orienting means C. Means C will be described in more detail hereinbelow.

Figure 3:
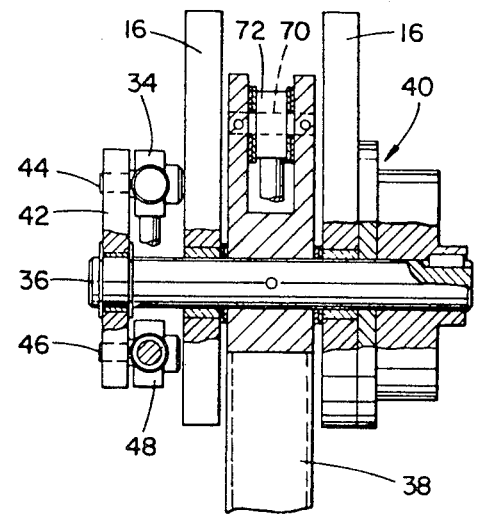
FIG. 3 is a cross-sectional view taken along lines 3—3 of FIG. 1.

Referring to FIGS. 1 and 3, arm 16 is drilled adjacent thereof spaced from first joint 17 to receive a pivot pin 36 which allows movement of the second arm relative to first arm 16 in the pitch plane. Pin 36 pivotally connects a second arm 38 of the overhead arm assembly to first arm 16 and is fixed to rotate with the second arm. Also operably interconnected with pin 36 and arm 16 is a third brake arrangement generally designated 40 constructed in accord with the first and second frictional brakes. An intermediate orientation means including a lever or bell crank 42 is rotatably mounted to pin 36 on the opposite end thereof from brake 40 and comprises a portion of orienting means C. Linear link 34 is pivotally connected at one end of bell crank 42 by a pin 44 and, as noted above, is also pivotally connected to clevis member 28 by pin 32 (FIG. 2). A linear link 48 for a second orientation connecting means is connected to the other end of the bell crank by a pin 46.

Figure 4:
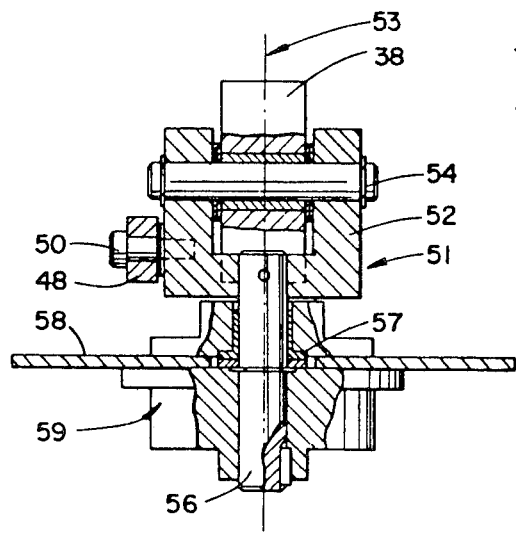
FIG. 4 is a cross-sectional view taken along lines 4—4 of FIG. 1.

As shown in FIG. 1, link 48 extends from the bell crank to a pivotal connection 50 located on the terminal or third arm 51 of overhead arm assembly B. Pivot connection 50 is on a clevis member 52 which comprises a part of the third arm. Terminal or third arm 51 which is shown in more detail in FIG. 4 has a central axis 53 along its length and is pivotally connected to the outermost end of second arm 38 through clevis member 52 by means of a pivot pin arrangement 54. The pivot pin is generally horizontally disposed to allow movement of the third arm in the pitch plane relative to first and second arms 16, 38.

Orientation means C includes a first parallelogram having the corners thereof defined by pins 20, 32, 44 and 36 with the opposite sides constrained to a parallel relationship with each other. The orientation means further includes a second parallelogram defined at its corners by pins 36, 46, 50 and 54 wherein the opposite sides are again constrained to a parallel relationship. Further, bell crank 42 which forms one side of each parallelogram acts as an intermediary to constrain the two parallelograms in a fixed relationship.

Using known geometric relationships, it will be seen that when there is relative movement between first and second arms 16, 38 or between arm 16 and column 10, the sides of the two parallelograms pivot about their corners. However, as the sides of the parallelograms pivot about their corners, the relative position of the pair of sides of each parallelogram interconnected by bell crank 42 remains fixed. That is, the side of the first parallelogram defined between pins 20 and 32, will remain in a fixed relationship with the side of the second parallelogram defined between pins 50 and 54. Thus, by selecting the appropriate relative positions for pivot pins 20, 32 and for pivot pins 50, 54, the central axis of terminal or third arm 51 may be maintained parallel to a vertical axis or in any other desirable orientation relative to the floor or to column 10. It will be appreciated that other specific arrangements for controlling the orientation of the terminal or third arm relative to the base could also be used. For example, gear wheels could be placed at pivots 20, 36 and 54 with flexible chains replacing the rigid links.

Referring again to both FIGS. 1 and 4, it will be seen that rotational coupling F facilitates rotation of manipulating means E about the central axis terminal arm 51 and includes a generally vertically disposed pivot pin 56 rigidly attached to clevis member 52. Pin 56 is rotatably mounted in a bushing 57 which is attached to a housing 58 of the displacement means G. A friction brake 59 of the type generally described above restrains the rotational movement displacement means G about pin 56 in a yaw plane.

The counterweight assembly D illustrated in FIG. 1 includes static and dynamic counterweights. The static counterweight 60 is affixed to first arm 16 at the end thereof adjacent joint 17, i.e., the lowermost or inner end of the arm. The dynamic counterweight includes a biasing means such as weight 62 mounted at the end of a lever 64 which itself is pivotally connected to first arm 16 by means of a pin 66. A linkage arrangement generally designated 72 defines a first counterweight connecting means. This linkage is pivotally connected to second arm 38 by a pin 70 and to lever 64 by a pin 68. It will be seen that pins 36, 66, 68 and 70 thus define the corners of a parallelogram. The longitudinal axis of lever 64 passes through pins 66, 68 and the longitudinal axis of second arm 38 passes through pins 36, 70. These axes form a pair of opposing parallelogram sides and accordingly, will be constrained in a parallel relationship to each other. Therefore, as arm 38 is pivoted about pin 36, lever 64 will be caused to pivot about pin 66 the same amount for causing the counterbalancing effect of assembly D to change as second arm 38 changes its angular orientation in space. Although the preferred embodiment here under discussion contemplates restraining lever 64 and arm 38 to a parallel relationship, it may be desirable in some circumstances to use other relationships. For some applications, it may be operationally advantageous to convert the dynamic counterweight assembly into a nonlinear application biasing means.

It will be appreciated that there will be many weight combinations between weights 60, 62 which will cause the arm to properly balance in the manner desired. One possible weight combination is that weight 60 be selected to cause main arm 16 to be balanced about pin 20. If lever arm 64 has the same weight as second arm 68 and has a length equal to the distance from pin 36 to pin 54, weight 62 would be selected to have the same mass as terminal arm 51 and manipulating assembly E depending from pivot pin 54. In this way, first or main arm 16 would be balanced about its pivotal connection with base A with both ends of the arm subjected to the same application of mass at the same lever arm length. It will be appreciated, however, that counterbalancing can be achieved by shortening lever 64 and increasing weight 62 or vice versa. Further, other distributions of weight between weights 60, 62 may be used along with changes in the position of weight 60 relative to the axis defined by pins 20, 36. One guideline for adjusting the relative weights and lever arm lengths is to maintain the moments of inertia about pins 66, 36 substantially constant about pin 20. Another guideline is to maintain the product of the mass and length of lever arm about the pivots substantially constant. A fabricated housing 74 is mounted on column 10 to advantageously shield persons from contact with counterweight assembly D and the end of arm 16.

Figure 5:
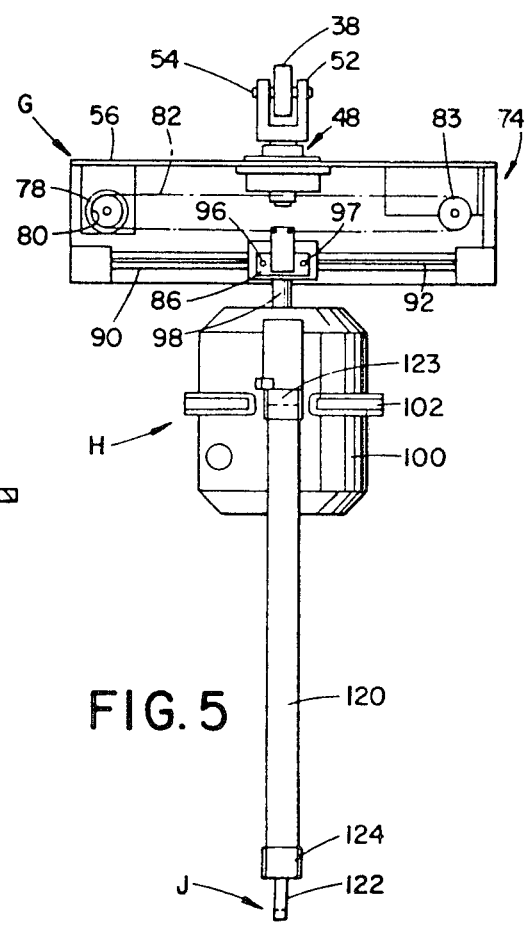
FIG. 5 is a front elevational view of the traversing mechanism shown in FIG. 1 with a portion thereof removed for ease of illustration.

Although a great variety of equipment may be attached to and depend from overhead arm assembly B, the preferred embodiment contemplates use of a manipulating assembly E adapted to move an ultrasonic probe in a single flat plane across or along a patient. As shown in FIGS. 1 and 5, displacement means G is attached to overhead arm assembly B by rotational means F. The displacement means includes a motor 76 coupled to a drive wheel 80 by an electric clutch 78. A continuous drive chain 82 is carried by wheel 80 and a companion wheel 83 and is connected to a flange 84 on a block or bracket 86. Block 86 slides on a rod 90 and convenient guide means such as a groove or track 92 for guiding the block along a linear path perpendicular to the axis of terminal arm 51. The guide means could alternatively comprise a cam follower or the like constrained between guide rods. Block 86 has a pair of detents which engage track 92. One detent 94 is best shown in FIG. 6 and comprises a sphere whose degree of engagement is set by a threaded shaft 96. The other detent is identical to detent 94 and is set by a threaded shaft 97 (FIG. 5). A suitable control (not shown) is provided for causing clutch 78 to engage and disengage. This control may advantageously include a displacement distance means for causing block 86 to be displaced a selectable or fixed incremental distance on each actuation of the clutch.

Referring to both FIGS. 1 and 5, a generally C-shaped arm bracket 98 connects the block to angular orientation selection means H and scan arm assembly I. A housing 100 connected with the arm bracket includes a handle 102 to facilitate positioning of the housing by the operator. Referring specifically to FIG. 1, angular orientation means H includes a pivot rod 104, a rotational rod 106 and a disc brake arrangement 108 to lock the angular rotation of rod 106 about the bracket 98. Rotational rod 106 allows orientation selection means H and scan arm assembly I to be selectively rotated thereabout in what is termed as a roll plane. A brake pad 110 attached to housing 100 is lightly in contact with one face of a brake disc 112 and a second brake pad 114 is movably engageable with the other face of brake disc 112 to selectively lock the rod 100 in a desired angular orientation within the rod plane. A screw handle 116 which threadably penetrates housing 100 and has brake pad 114 affixed to the innermost end thereof allows the operator to screw the pad firmly into contact with disc 112 to achieve such locking. A friction type of brake arrangement could also be used in place of disc brake arrangement 108.

Pivotally attached to rod 106 by a pin 117 is a multijointed scan arm assembly I. In the preferred embodiment, the scan arm assembly comprises three pivotally joined arms 118, 120 and 122. First scan arm 118 is constrained at one end by pin 117 to pivot about rod 106 only in a single scan plane. The orientation of the scan plane is dictated by the rotational orientation of rod portion 106. One end area of scan area arm 120 is pivotally attached to the other end of first scan arm 118 by a pin 123. Third scan arm 122 is attached to the other or second end of the second scan arm at a pivot joint 124. Detachably connected to scan arm 122 is a transducer head J. The pivot connections at 123, 124 are such that third scan arm 122 is constrained to move only within the scan plane. Moreover, these pivot connections may, if desired, also include friction brakes similar to those discussed hereinabove. Alternately, for some applications, joint 124 may advantageously comprise a gimbal.

Figure 7:
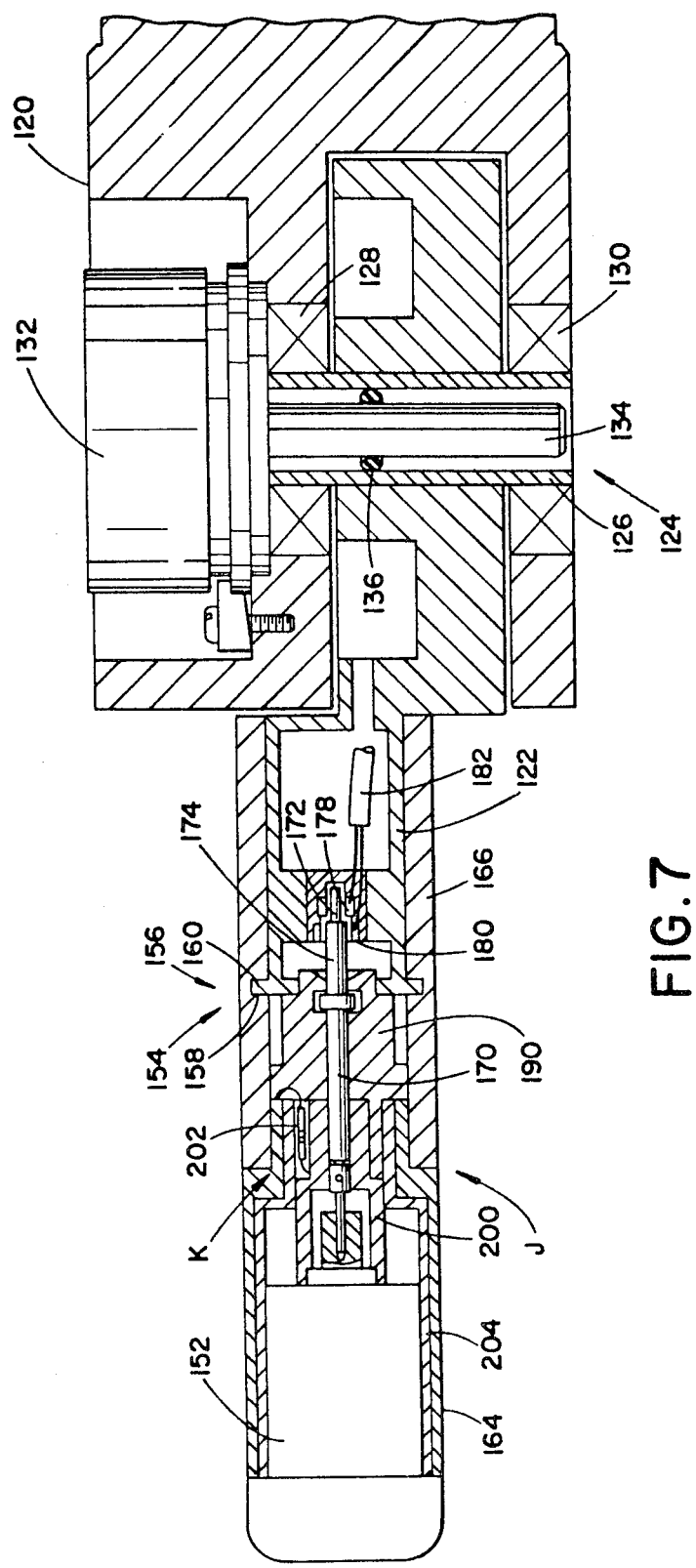
FIG. 7 is a cutaway view of a transducer head and scan arm.

The pivotal joint 124 is shown in more detail in FIG. 7. Rigidly connected for rotation with third scan arm 122 is a cylindrical axle 126. Axle 126 is received in a pair of bearings 128 and 130 which are connected with second scan arm 120.

For monitoring the angular displacement between scan arms 120 and 122, a potentiometer or variable resistance 132 is mounted in arm 120. A shaft 134 of the potentiometer which varies its resistance through rotational movement is positioned concentrically with cylindrical axle 126. A resilient connecting means 136 interconnects shaft 134 and axel 126 so that angular displacement of arm 120 relative to arm 122 causes a similar rotation of shaft 134. Resilient connecting means 136 may take the form of a rubber O-ring.

Similar cylindrical axle and potentiometer arrangements can be used to determine the angular orientation between other pivoted arms in the assembly. The change in the resistance of the potentiometers may be transformed into an indication of transducer position and angle using the techniques shown in the article "Ultrasonic Contact Scanner for Diagnostic Application", supra.

Second scan arm 120 has a section 138 which extends above pin 123 as viewed in FIG. 1 to a pivotal connection 140. A scan arm dynamic counterweight assembly which includes a connecting rod 142 extends between connection 140 and a pivot pin 144 in a lever arm 146. Lever arm 146 is pivotally attached at one end to first scan arm 118 by a pin 148 and has a biasing means such as a counterweight 150 disposed at the other end. Connecting rod 142 constrains lever arm 146 and arm 120 to a substantially parallel or other fixed relationship relative to each other.

Weight 150 with lever arm 146 provides a dynamic counterbalance with functions in a manner similar to that described above with reference to the dynamic counterbalance portion of assembly D. It will be noted that pivot connections 148, 123, 140 and 144 define a parallelogram with sides of a fixed length. Accordingly, this parallelogram constrains lever arm 146 to remain parallel to second scan arm 120.

Ultrasonic probe or transducer head J may include a single one or an array of electroacoustic transducer elements 152 used for ultrasonic diagnostic testing. Such transducers are known and do not themselves comprise a part of the present invention. They produce ultrasonic sound waves which are broadcast at a known angle relative to the central axis of the third scan arm and receive ultrasonic echoes from interfaces in a patient. By coordinating the position and orientation of the transducer with an electronic processing unit, the precise origin of the received ultrasonic echoes within the patient's body can be determined. The ultrasonic scanning device can then accurately produce an image of the subsurface region of the patient.

Referring again to FIG. 7, the transducer head J includes a first coupling means 154 for mechanically and electrically coupling the transducer head on third scan arm 122. Third scan arm 122 includes a second coupling means 156 for mechanically and electrically coupling the arm with transducer heads. The first and second coupling means are designed to interconnect to form a physical and electrical connection. In the preferred embodiment, the first and second coupling means include a bayonet-type fastening structure including a groove 158 in the first coupling means for receiving a shoulder 160 of the second coupling means. The shoulder and groove are metallic, in the preferred embodiment, to provide not only a strong physical connection but an electrical ground connection.

The first and second coupling means provide further electrical connection between each transducer head and the scan arm. In particular, the first coupling means further includes coaxial conductor 170 which carries an inner electric contact 172 electrically interconnected with the transducer, and an outer electric contact 174 electrically interconnected with the identification means K. The second coupling means further includes a pair of female electric contacts 178 and 180 for making electrical connection with contacts 172 and 174 respectively. An output cable 182 connects contacts 178 and 180 with an operator control panel.

A spacer 190 made of an electrically insulating material maintains coaxial center conductor 170 physically and electrically spaced from the common ground of the outer bodies. Further, spacer 190 holds the center conductor in alignment with female electric contacts 178 and 180 along a central axis of the transducer head.

The identification means K includes an inside electrically conductive shield 200 which is mounted around center conductor 170 so as to make electric contact with the outer conductor thereof. Mounted on the inside shield is an identification circuit which may be composed of active or passive circuit elements. Active circuit elements, such as transistors, are chosen to produce a characteristic electric response to a fixed excitation from the identification system. The response may, for example, be the oscillation frequency of an oscillator. Passive circuit elements, such as capacitors, inductors and resistors, are chosen to produce a characteristic impedance. In the preferred embodiment, an impedance assembly 202 of passive circuit elements is connected between shield 200 and the common ground of outer body 164. Specifically, in the preferred embodiment, the impedance assembly is a resistor. In each type of transducer head, the resistor has a characteristic resistance. An indicia of the characteristic resistivity of resistor 202 is provided by applying an electric field to it and measuring the change in the electric field.

An insulator shield 204 insulates the inside shield 200 from the common ground of outer body 164.

FIG. 8 shows an embodiment of the transducer head identification system and the impedance assembly 202 which is a part of the identification means K located in each transducer head.

A means 210 for applying an electric field across the impedance assembly produces an electric signal indicative of the impedance of the impedance assembly 202. In the preferred embodiment, means 210 is a current source which, when applied to impedance assembly, produces an analog voltage proportional to the impedance of assembly 202. Other means, such as a voltage divider, could be used.

Impedance determination means L receives this analog voltage signal at an impedance buffer 212. An analog-to-digital converter 214 converts the analog voltage representation of the impedance to a digital representation. An 8-bit analog-to-digital converter would allow the identification system to differentiate among 28, i.e. 256, transducer heads. A tristate buffer 216 connects the digital representation to a multiplexer 218 which serializes the digital representation. The serialized data is conveyed through an AND gate 220 which permits or blocks the flow of serialized data on command to generating means M.

Generating means M includes a character generator 230. The character generator in reponse to each input produces one or more alpha-numeric characters. The characters may specify the number of the transducer head, or may indicate characteristics of the transducer head, e.g., focal length or other information. The characters are displayed on a cathode ray tube or video monitor 232. More precisely, the characters are displayed along the margin as the ultrasonic image is simultaneously displayed on the center of the CRT display.

The generating means may also generate alpha-numeric characters to represent other information. A source 240 of other electric signals is converted by an analog-to-digital converter 242 to a digital representation of the other information. The digitized other information is connected through a second tristate buffer 244 to multiplexer 218. The other information signals can be used to cause the character generator 230 to generate the patient's name or identification code, the angle of the scan plane or other pertinent information.

A timing and control means 250 controls the analog-to-digital convertors and tristate buffers to control the system timing and to block one or both of the signals from causing an alpha-numeric display from being generated.

In operation, overhead arm assembly B with attendant equipment is brought into close proximity with the patient who is positioned therebeneath. Normally, the patient lies horizontally on a platform or table so that a traverse section of his body can be examined. However, other orientations may also be used if necessary and/or desirable.

The operator selects the transducer head which he wishes to use and snaps it into the third scan arm. The operator then grasps handle 102 on means H for moving manipulating assembly E to the appropriate position and height for, in turn, positioning scan arm assembly I to make a proper scan. This appropriate position is such that the plane of movement of the scan arm assembly is coplanar with the plane of interest in the patient. The appropriate height is that distance above the patient such that the operator can easily position probe P at a multiplicity of points along the line of intersection between the plane and the surface of the patient and then rock third scan arm 122 about pivot 124 at each point of contact. This action will be described in greater detail hereinafter.

As the operator swings manipulating assembly E into position, a number of movements occur. The overhead arm assembly B rotates in the yaw plane about pin 18. A second yaw plane rotation occurs in rotational connection F. Once positioned, friction brakes 24, 26 and 59 retain the manipulating assembly in this selected yaw plane orientation. Additionally, the operator rotates the scan arm assembly in the roll plane about pin 104 with the orientation of this roll plane retained by means of brake 108.

In selecting the height and the distance from column 10, the operator pivots arms 16, 38 and 51 in the pitch plane about pivot pins 20, 36 and 54. As discussed above, during the pitch plane positioning, orientation means C constrains the central axis of arm 51 to a vertical disposition. Once positioned, friction brakes 30, 40 help retain overhead arms 16, 38 and 51 in that position.

The ease with which the overhead arms can be moved and their stability in the selected position is increased by counterbalance means D. As also discussed above, the pivoting of arm 16 about pivot pin 20 varies the effective lever arm with which counterweight 60 is applied. Pivoting of arm 38 about pivot pin 36 relative to arm 16 varies the lever arm of dynamic counterweight 62. Proper selection of weights 60, 62 coupled with proper selection of the length of lever 64 will cause the manipulating assembly to appear or seem to be substantially weightless to the operator when it is being positioned to accommodate a scan.

With the overall assembly properly positioned, the operator moves the transducer head J along the intersection of the scan arm movement plane and the body surface of the patient. As the probe traverses the patient, the operator oscillates it about the point or area of patient contact so that the internal area of the patient can be "viewed" from a multiplicity of directions. Conventional ultrasonic image reconstruction equipment may be used for this purpose and such equipment does not itself from a part of the present invention. However, one type and arrangement of suitable equipment is shown and described in the article by Joseph Holmes, et al., "Ultrasonic Contact Scanner for Diagnostic Application", supra. The arrangement therein shown includes circuitry for monitoring the position and orientation of the transducer head and for processing the ultrasonic echo signals to produce an image of the planar patient section examined.

The ultrasonic image is displayed on the monitor 232 as well as an alpha-numeric representation indicating the transducer head used and other information.

After the first scan image is produced and recorded, the operator actuates clutch 78 arrangement of displacement assembly G for allowing motor 76 to move the plane of examination by a known increment to a new position. Because of the construction of assembly G as described in detail hereinabove, the plane of the new position is parallel to the plane of the original position. The scanning procedure is then repeated in this second plane and in as many further incrementally shifted planes as may be desired. This series of scans produces a series of images representing parallel sections of the patient.

It is understood that the present invention may be used to carry other work elements that require precise positioning and movement. For example, instead of using an ultrasonic transmitting and receiving probe, the system can carry an electron or laser welding unit for making precise welds, carry engraving tools or carry other precision equipment.

The above physical embodiment is presented only by way of example and not for purposes of limitation. The invention includes not only the above specific embodiment, but all the embodiments thereto as set forth in the claims as follows.

We claim:
1. A pivot assembly comprising:
   (a) bearing means mounted to a first arm;
   (b) a cylindrical axle rotatably mounted in said bearing means and fixedly mounted to a second arm;
   (c) a potentiometer having a rotatable shaft for varying the resistance of the potentiometer, said potentiometer fixedly mounted to said first arm and the rotatable shaft disposed along the axis of said cylindrical axle; and
   (d) resilient connecting means for connecting said shaft and said axle whereby said shaft and said axle rotate together.
2. The assembly as set forth in claim 1 wherein said connecting means is a rubber O-ring.

* * * * *